United States Patent [19]

Bommarito

[11] 4,381,143

[45] Apr. 26, 1983

[54] OPHTHALMIC TEST LENS HOLDER

[76] Inventor: Paul F. Bommarito, 10684 Martinwood Way, Cupertino, Calif. 95014

[21] Appl. No.: 179,807

[22] Filed: Aug. 20, 1980

Related U.S. Application Data

[63] Continuation of Ser. No. 6,340, Jan. 25, 1979, abandoned.

[51] Int. Cl.³ .............................................. A61B 3/04
[52] U.S. Cl. .......................................... 351/230; 351/225
[58] Field of Search .................................... 351/19–22, 351/57, 58, 26

[56] References Cited

U.S. PATENT DOCUMENTS

| | | |
|---|---|---|
| 1,661,967 | 3/1928 | Savoie . |
| 1,949,449 | 3/1934 | Broomfield ............................ 88/41 |
| 2,006,645 | 7/1935 | Masters .................................. 88/41 |
| 2,384,233 | 9/1945 | Bishop ................................... 88/41 |
| 2,467,343 | 4/1949 | Street ..................................... 351/19 |
| 2,842,029 | 7/1958 | Roth ....................................... 88/41 |
| 3,446,548 | 5/1969 | Rummel et al. ....................... 351/58 |

OTHER PUBLICATIONS

"Jannelli Clip", Signet Optical Corporation, Signet Optical Corporation Publication.
"Rodenstock Interpupillary Gauge", Rodenstock Gauge Brochure.
"Bi–Fo–Rite . . . ", Bi–Fo–Rite Brochure.
Halbert Trial Clip, Keeler, Jun. 1972.

Primary Examiner—John K. Corbin
Assistant Examiner—Rodney B. Bovernick
Attorney, Agent, or Firm—Thomas Schneck

[57] ABSTRACT

A lens holder having a pair of spring connected clamping members with apertures therein mountable over a lens socket of spectacle frames. The clamping members have an extent which is sufficient to completely span lens sockets and extend a distance beyond. Transverse lateral rulings on at least one of the clamping members permit gauging an aperture in a clamping member relative to a socket in a spectacle frame. In this manner, geometrical characteristics of a test lens may be measured and recorded for the purpose of making permanent lenses for a selected spectacle frame. In addition to transverse lateral rulings on a clamping member, angular rulings about an aperture in a clamping member may also be applied for determining angular orientations of a test lens.

11 Claims, 9 Drawing Figures

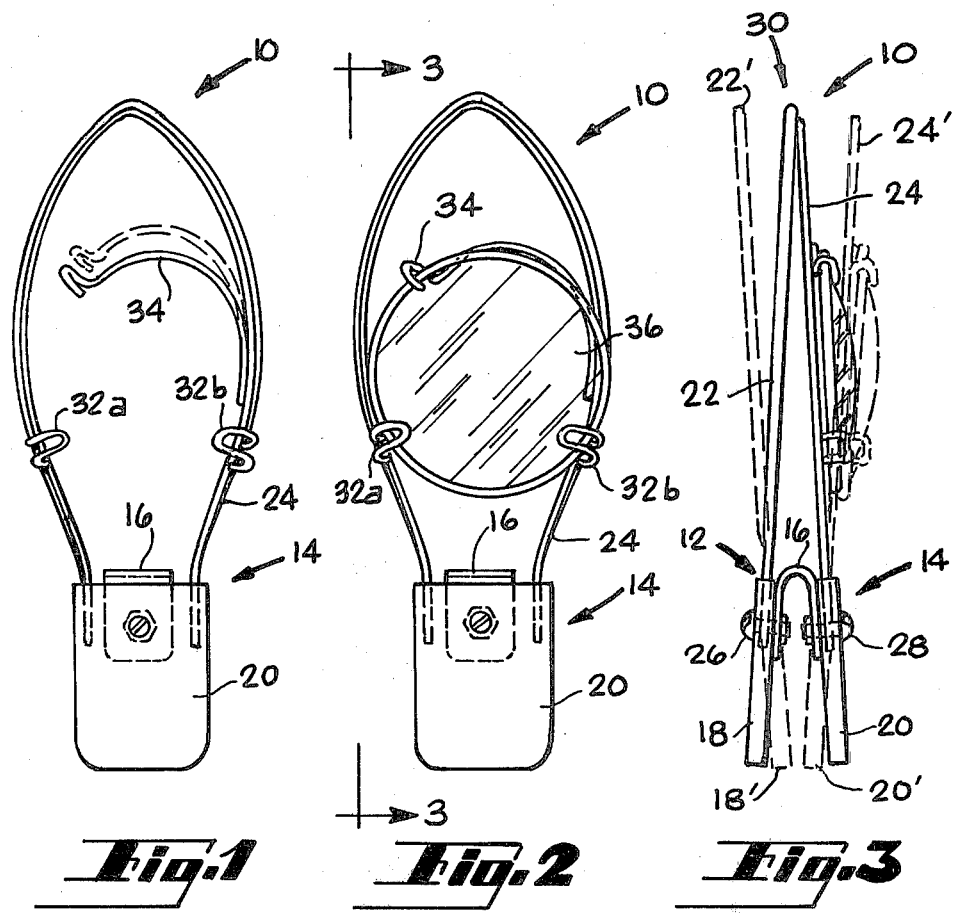
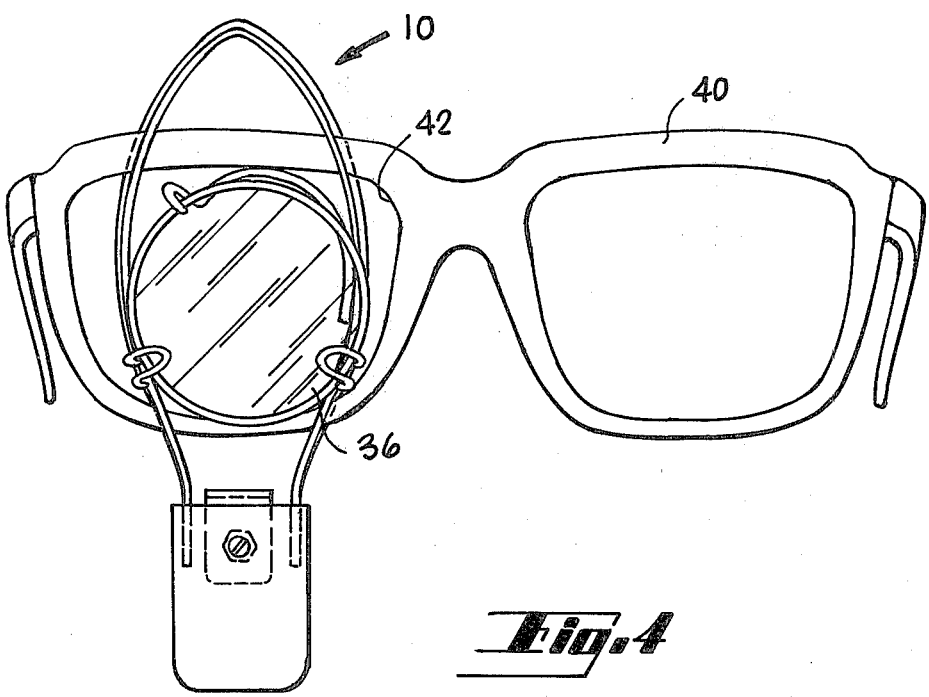

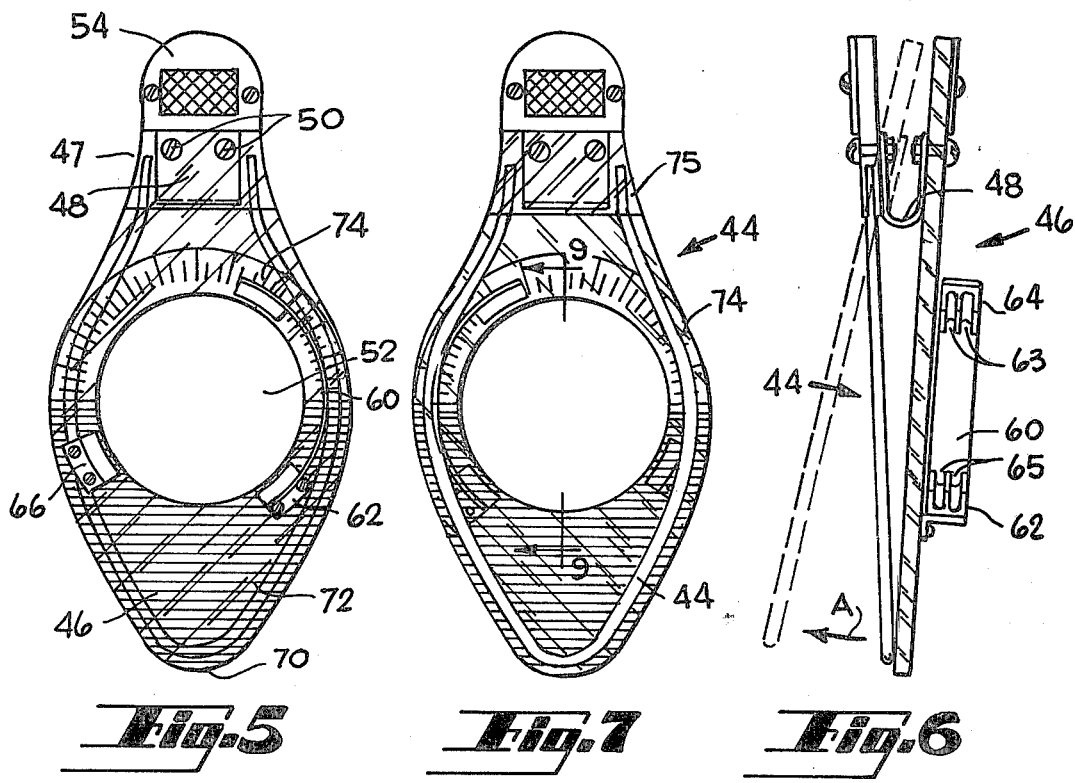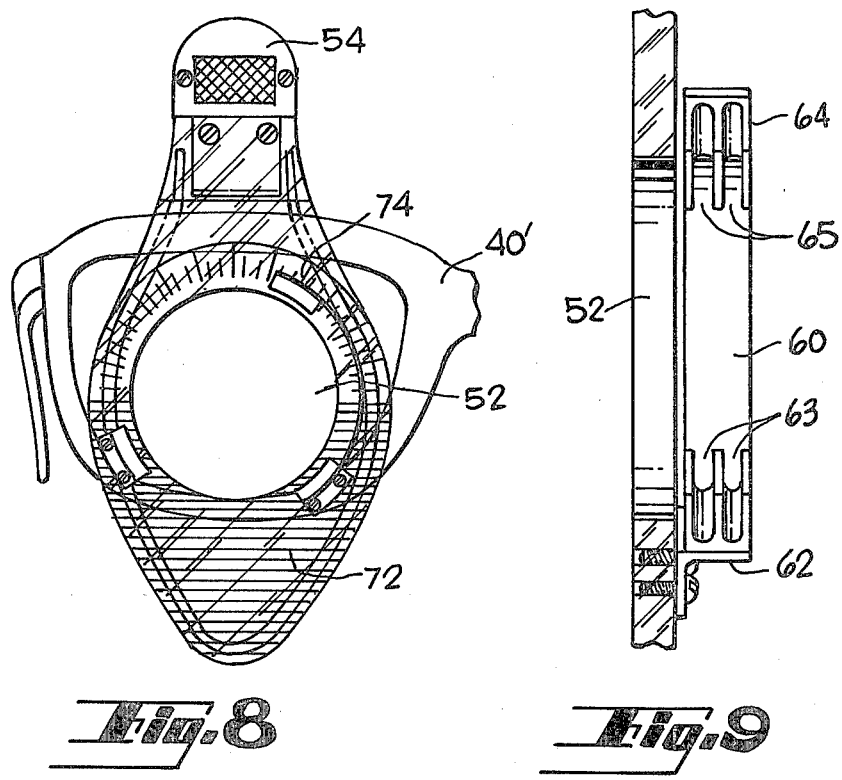

OPHTHALMIC TEST LENS HOLDER

CROSS REFERENCE TO RELATED APPLICATION

This is a continuation-in-part of application Ser. No. 6,340, filed Jan. 25, 1979, now abandoned.

BACKGROUND OF THE INVENTION a. Field of the Invention

This invention relates generally to lens holders and more particularly to devices for temporarily attaching a lens to a pair of spectacle frames for measuring and testing purposes.

b. Prior Art

Ophthalmic practitioners utilize many specialized testing devices in the category of lens holders. One such device is the "Janelli Clip" which basically includes a pair of lens holders with cylindrical channels for eye pieces that form a number of test lens wells. The ophthalmic practitioner places one or more test lenses in the lens wells to test a prescription or to demonstrate a change in prescription or for other purposes.

Another piece of equipment used by ophthalmic practitioners is a clip-on device which tests for bifocal line placement in a bifocal correction lens. One such apparatus includes a pair of simulated opaque bifocal shaped members positioned over the lens sockets of an empty pair of spectacle frames by a pair of plastic spring clips. The height of each of the bifocal type lenses may be then adjusted by the practitioner or by the patient until the patient is satisfied with its position. The position of the two test lenses is then noted so that the bifocal line of the permanent lenses will be correctly positioned.

There are also a number of corrective devices, similar to the above mentioned bifocal test clip, but not used for testing, that can be attached to an existing pair of eyeglasses to supplement or modify the refractive property of the permanent lenses. These devices typically include relatively small lenses that are adjustably or removably attached to the frames of the glasses, and may be either prescribed by the refractionist or may be purchased by the consumer in an over-the-counter situation. Examples of these devices are found in U.S. Pat. Nos. 1,661,967 of J. Savoie, 1,949,449 of F. Broomfield, 2,006,645 of C. Masters, 2,384,233 of A. Bishop, 2,842,029 of A. Roth and 3,446,548 of W. Rummel, et al.

Besides measuring and testing lens prescriptions, an ophthalmic practitioner frequently desires to show a patient the appearance of frames, without lenses, on his or her face. Often, the patient cannot see well enough to view him or herself in a mirror without corrective lenses. It is an object of this invention to provide an ophthalmic device which can temporarily attach a test lens to a pair of spectacle frames so that a patient can see what the frames look like as he or she is wearing them.

Another object of the invention is to provide a combination device which can be used both to hold test lenses to a pair of spectacle frames with and without a prescription lens and which can be used to determine the correct placement of the bifocal line of a permanent eyeglass lens.

Another object of the invention is to demonstrate a new prescription in a spectacle frame or to show the change in prescription over the patient's old prescription.

SUMMARY OF THE INVENTION

The above objects have been met with a pair of elongated clamping members resiliently attached together near one end so that their other ends are biased towards one another, and a test lens holding bracket attached to one of the clamping members. The clamping members temporarily fasten the device to a pair of spectacle frames so that a test lens, held by the bracket, is positioned before a lens socket. The clamping members extend beyond a lens frame so that at least one of the clamping members can bear rulings which indicate distance and angles for the purpose of adjusting lenses with respect to a frame, for example, the height of a bifocal line relative to the frame socket.

An advantage of this invention is that its uncomplicated structure provides for an inexpensive but durable device for temporarily attaching a test lens to a pair of spectacle frames.

Another advantage of this invention is that the patient can look through a test lens clamped over an empty lens socket of the frame so that he or she can tell what the spectacle frames will look like when wearing them. Since the test lens holder can be quickly clipped on and off of a pair of frames, many different frames can be rapidly viewed by the patient.

A further advantage of this invention is that, in one embodiment, a test lens holder and a bifocal line positioning device are integrated into a single unit.

BRIEF DESCRIPTION OF THE DRAWINGS

FIG. 1 is a front elevational view of an ophthalmic test lens holder in accordance with the present invention.

FIG. 2 is a front elevational view similar to the one of FIG. 1 illustrating a test lens held to one of the clamping members of the device.

FIG. 3 is a side elevational view as seen along line 3—3 of FIG. 2.

FIG. 4 illustrates the lens holder of FIG. 2 attached over a lens socket of a pair of spectacle frames.

FIG. 5 is a front elevational view of an alternate embodiment of an ophthalmic test lens holder in accordance with the present invention.

FIG. 6 is a side operational view of the holder of FIG. 5.

FIG. 7 is a back elevational view of the ophthalmic test lens holder of FIG. 5.

FIG. 8 shows the test lens holder attached over a lens socket of spectacle frames.

FIG. 9 is a side detail view taken along the lines 9—9 in FIG. 7.

DESCRIPTION OF THE PREFERRED EMBODIMENT

Referring to FIGS. 1-3, an ophthalmic test lens holder 10 is shown to include a first clamping member 12 attached to a second clamping member 14 by a U-shaped compression spring 16. In this embodiment, clamping members 12 and 14 include a base portion 18 and 20, respectively, to which is attached an elongated loop of wire 22 and 24, respectively. The area of space inwardly bounded by the loops of wire define a viewing aperture, as will be discussed in greater detail subsequently. It is not necessary to use wire, but strong, flexible materials are preferable. Many plastics are acceptable.

U-shaped compression spring 16 is connected to base portion 18 by a fastener assembly 26 and is connected to base portion 20 by a fastener assembly 28. The compression spring serves to bias the ends 30 of the clamping members together, as shown in solid lines in FIG. 3. When base portions 18 and 20 are pressed together, usually between the thumb and forefinger of the practitioner's hand, so as to be positioned at 18' and 20', the ends 30 of the elongated loops of wire will spread apart as shown at 22' and 24'. When pressure is removed from the base portions, spring 16 will return the clamping members to their original, closed positions. Thus, as configured, lens holder 10 is constructed to have a clip-like action, as will be more fully discussed later with reference to FIG. 4.

Attached to loop 24 is a test lens bracket which, in this embodiment, includes a pair of bracket pieces 32a and 32b and an elongated spring bracket piece 34. As best seen in FIG. 2, a test lens 36 can be held to loop 24 by placing it against the pair of bracket pieces 32a, 32b and by latching the hooked end of spring bracket piece 34 over the top of it. The spring bracket piece exerts a sufficient force upon the lens to securely hold it against the pair of bracket pieces 32.

The ophthalmic test lens holder 10 as described above may be constructed from a wide variety of materials. The base portions 18 and 20 can be formed from metal, plastic or other materials, although plastic is preferable for large scale production. The elongated loops of wire are preferably formed from a strong, resilient material such as spring steel. Spring bracket piece 34, of course, would have to be formed from spring steel or from some other rugged spring material.

Either or both of the elongated loops may be covered or coated with a material having a higher coefficient of friction than that of the loop material itself so as to help prevent the test lens holder from slipping when clamped to a pair of spectacle frames. In this preferred embodiment, elongated loop 22 is coated by a dip applied plastic material.

With reference to FIG. 4, the operation of ophthalmic test lens holder 10 can be discussed. As it is most normally used, test lens holder 10 is clamped to a pair of empty spectacle frames 40 by pressing the base portions between the thumb and forefinger to separate ends 30, by disposing the clamping members on either side of a lens socket, and by releasing the pressure on the base portions. The bottom of a test lens is usually aligned with the bottom of a lens socket in a pair of spectacle frames if the position of a bifocal line is to be measured. The spectacle frames are placed on the face of a patient so that he or she can look at a mirror through the test lens held by the test lens holder.

Referring now to FIGS. 5-9, another embodiment of a test lens holder is shown. In this embodiment, a first clamping member 44, seen in FIG. 6, is connected to a second clamping member 46 by a U-shaped compression spring 48 in a manner analogous to that of the previous embodiment. In this embodiment, at least one of the clamping members 44 or 46 is constructed from an elongated piece of flat, transparent plastic material which has a general overall shape similar to the loop, previously described and having a viewing aperture 52 in the center thereof, shown in FIG. 5, which is a round hole slightly smaller than a test lens, but approximately the same size. Clamping member 46 has a length which is greater than the distance across any socket of a spectacle frame. Preferably, the member is at least 30% greater than the vertical distance across a spectacle frame. Attached to the base portion 47 of member 46 is a thumb plate 54. Base portion 47 is used to secure spring 48 thereto by means of fasteners 50.

The test lens support bracket consists of an arc-shaped spring 60 which is fastened to member 46 by an L-shaped pad 62 on one side, as seen in the detail of FIG. 9. At the opposite end of the bracket is a guide pad 64 which is free to move at the end of spring 60. Pads 62 and 64 have grooves 63 and 65 adapted to receive a test lens. While only two grooves are shown, more grooves can be provided if desired. The number of grooves is not critical. The reason that additional grooves may be desired is that it is very common for a practitioner to use two or more lenses to help determine the exact specification of a permanent correction lens. The grooves 62 and 65 are intended to lie in a semicircular arc since test lenses are usually circular. A test lens is held against a third pad 66, seen in FIG. 5, which is on the opposite side of aperture 52 with respect to spring 60. The pad 66 also has a corresponding number of grooves therein for seating test lenses. The grooves may be either machined into the pads or molded. It is preferable to have at least one groove, usually the outermost, with a greater thickness compared to the innermost groove to accommodate thicker lenses, such as those having greater corrective power for the near-sighted.

The member 46 has a portion extending from the middle of lens aperture 52 to a point 70, well below the furthest downward extent of lens aperture 52. This portion is necessary for two reasons. First, it allows the test lens holder to completely span a lens socket, for even the largest of spectacle frames. Secondly, the downwardly extending portion of the member, opposite the base bears a number of lateral rulings 72 which are used for marking distances of a test lens relative to the socket. The rulings may include indicia identifying individual rulings or groups of rulings. For example, rulings may be marked indicating millimeter or other distance intervals.

One of the chief uses of the lateral ruling 72 is to indicate bifocal segment height relative to the bottom of a lens socket in a frame. An ophthalmic practitioner can first place the bottom of lens aperture 52 to coincide with the bottom of the socket in a spectacle frame. Then, by moving the ophthalmic test lens holder of the present invention upwardly or downwardly, he can count the number of rulings or gauge the distance that a bifocal segment line should be placed with respect to the bottom of the spectacle frame. Usually, a patient indicates a desired bifocal segment line height. This height can be accurately gauged by the present invention. The lateral rulings are parallel to each other and when used, are generally parallel to the direction of the bridge of spectacles, although this orientation is not the only possible one. The rulings may be engraved, painted or otherwise applied to base portion.

While the extended tip portion of the member carries distance rulings 72, the side of the member toward the base 47 carries angular rulings 74 which are used to indicate angular orientation of a test lens, for measuring the angular alignment of a test lens, as in astigmatism correction.

With respect to FIG. 7, the backside of the ophthalmic test lens holder of FIG. 5 may be seen. In this case, the back member has the clamping member 44 which consists of a wire loop 73 held by base portion 75. The wire loop 73 may be constructed in a manner similar to loop 24 in FIG. 1. While a wire loop is shown as the back clamping member, a second plastic clamping member, similar to member 46 may also be used. A wire member is preferred for the backside, because it is light weight and may be made relatively thin, so as not to cause discomfort to a patient.

FIG. 8 shows the test lens holder of FIGS. 5-7 positioned over a spectable frame 40'. The base of aperture 52 is aligned with the bottom of the socket of the frame and then the lateral rulings 72 are observed to measure the desired location of a lens feature, such as a bifocal segment line height. Angular alignment measurements are observed by reading the angular rulings 74 in a similar manner. The test lens holder may be moved by pressure against the thumb plate 54 relative to an index finger plate 55 on the back member 44. This causes spring compression and an opening of the frame as indicated by the arrow A in FIG. 6. The test lens holder may be moved up or down as required by the practitioner or patient until desired measurements may be made. Note that it is important that the length of the holder in the vertical direction be sufficient to allow upward movement of a test lens across the socket of a frame. For example, in the situation where a patient desires a relatively high bifocal line, a relatively small test lens must be supported in a high position relative to a big socket in a large frame. FIG. 8 illustrates a medium size frame with a typical small test lens size. With larger frames, the test lens holder must have a length below the lens aperture of at least one centimeter and preferably two to four centimeter.

With the test lens holder of this embodiment, it is possible for a practitioner to perform three important and distinct tests. First, the practitioner can determine by means of one or more test lenses exactly what the correctional formula for the permanent eyeglass lenses should be. Secondly, he is able to determine exactly where to place the bifocal line prior to the preparation of a permanent lens. Finally, the patient is allowed to view a number of frames with lenses equivalent to his regular prescription so that he can judge the frame style, even though the frames are without lenses.

What is claimed is:

1. An ophthalmic test lens holder for use with spectacle frames comprising,
    an elongated first clamping member defining a first aperture therein,
    an elongated second clamping member, generally the same size as the first clamping member and defining a second aperture therein, said second clamping member facing said first clamping member and spaced therefrom a distance accommodating a spectacle frame therebetween, with said first aperture and said second aperture aligned to transmit light therethrough, said first and second clamping members being elongated and having an extended tip with a clamping member length substantially greater than a lens socket in the spectacle frame intended to be placed between said clamping members such that the clamping members may adjustably be disposed across and contact opposed sides of a lens socket of said spectacle frame, spanning the dimension of the socket, the first of said clamping members having a plurality of parallel lateral rulings thereon, for referencing an aperture relative to the socket, the number and extent of lateral rulings being sufficient to reference the position of a test lens held over an aperture with respect to said socket,
    spring means connected to said first and second clamping members for resiliently biasing said first clamping member toward said second clamping member, and
    bracket means attached to one of said clamping members for removably holding a test lens over said second aperture.

2. The ophthalmic test lens holder of claim 1 wherein said first clamping member having said transverse rulings has angular rulings about an aperture.

3. The ophthalmic test lens holder of claim 1 wherein said second clamping member includes a base portion and an elongated rigid wire loop with loop ends attached to said base portion.

4. The ophthalmic test lens holder of claim 1 wherein said first clamping member is transparent.

5. The ophthalmic test lens holder of claim 1 wherein each clamping member has a base portion, including an area for placement of a human finger, said base portion being opposite said extended tip.

6. The ophthalmic test lens holder of claim 1 wherein at lest some of said lateral rulings are on the extended tip of said second clamping member.

7. An ophthalmic test lens holder for use with spectacle frames comprising,
    a first clamping member having a base portion supporting an elongated wire loop, the wire loop having two fixed lens supports and a spring bracket support, said supports holding a test lens in place, the lengthwise dimension of the elongated wire loop substantially exceeding the dimension of a lens socket of spectacle frames, and
    a second clamping member aligned with and substantially similar to the first clamping member but without said bracket pieces, said first and second clamping members connected at respective base portions by a spring resiliently biasing said first and second clamping members together but allowing a spectacle frame to be interposed therebetween whereby an ophthalmic test lens supported in said first clamping member may be moved about the lens socket of the spectacle frame.

8. An ophthalmic test lens holder for use with spectacle frames comprising,
    a first clamping member having a base portion supporting an elongated wire loop, the lengthwise dimension of the elongated wire loop substantially exceeding the dimension of a lens socket of spectacle frames, and
    a second clamping member having a base portion and an elongated transparent portion supported by the base portion, the shape of the transparent portion similar to the elongated wire loop, the transparent portion having an aperture defined therein approximating the size of a test lens, and having two fixed lens supports and a spring bracket support, said supports disposed about said aperture for holding a test lens in place over said aperture, said first and second clamping members connected at respective base portions by a spring resiliently biasing said first and second clamping members together but allowing a spectacle frame to be interposed therebetween whereby an ophthalmic test lens supported in said second clamping member may be moved about the lens socket of the spectacle frame.

9. An ophthalmic test lens holder for use with spectacle frames comprising, an elongated first clamping member defining a first aperture therein, an elongated second clamping member, generally the same size as the first clamping member and defining a second aperture therein, said second clamping member facing said first clamping member and spaced therefrom a distance accommodating a spectacle frame therebetween, with said first aperture and said second aperture aligned to transmit light therethrough, said first and second clamping members being elongated and having an extended tip with a clamping member length substantially greater than a lens socket in the spectacle frame intended to be placed between said clamping members such that the clamping members may adjustably be disposed across and contact opposed sides of a lens socket of said spectacle frame, spring means connected to said first and second clamping members for resiliently biasing said first clamping member toward said second clamping member, and bracket means attached to one of said clamping members for removably holding a test lens over said second aperture.

10. An ophthalmic test lens holder comprising, a first elongated clamping member having a first base portion of a size accommodating a finger and a lens portion adjacent to said base portion, said lens portion having an elongated dimension substantially exceeding the vertical distance across spectacle sockets, said lens portion having a first aperture therein approximately the size of a test lens, said lens portion having bracket means adjacent said aperture for holding a test lens over the aperture, a second elongated clamping member facing the first elongated clamping member and having a second base portion similar to the first base portion and a backing portion adjacent to said base portion having an elongated dimension similar to said lens portion of the first elongated clamping member, said backing portion having a second aperture therein at least as great as said first aperture, said second elongated clamping member spaced from the first clamping member a distance slightly greater than the thickness of spectacle sockets and joined thereto by spring means biasing the lens portion of the first member to the backing portion of the second member, one of said clamping members having indicia means for referencing the position of a test lens relative to a socket positioned between said members.

11. The ophthalmic test lens holder of claim 8 wherein the length of said members exceeds the vertical distance across a spectacle frame by at least 30%.

* * * * *